(12) United States Patent
Audousset

(10) Patent No.: US 6,395,042 B1
(45) Date of Patent: May 28, 2002

(54) COMPOSITION FOR THE OXIDATION DYEING OF KERATIN FIBERS AND DYEING PROCESS USING THIS COMPOSITION

(75) Inventor: Marie-Pascale Audousset, Asnieres (FR)

(73) Assignee: L'Oréal, Paris (FR)

(*) Notice: Subject to any disclaimer, the term of this patent is extended or adjusted under 35 U.S.C. 154(b) by 0 days.

(21) Appl. No.: 09/443,141

(22) Filed: Nov. 19, 1999

(30) Foreign Application Priority Data

Nov. 20, 1998 (FR) .................................. 98 14653

(51) Int. Cl.$^7$ ................................................ A61K 7/13

(52) U.S. Cl. ........................ 8/409; 8/408; 8/410; 8/423

(58) Field of Search ............................ 8/408, 409, 410, 8/423

(56) References Cited

U.S. PATENT DOCUMENTS

| | | |
|---|---|---|
| 3,061,432 A | 10/1962 | Menzel et al. |
| 3,227,554 A | 1/1966 | Barr et al. ................. 430/382 |
| 3,419,391 A | 12/1968 | Young ........................ 430/387 |
| 3,690,810 A * | 9/1972 | Bugaut et al. ................. 8/409 |
| 3,705,896 A | 12/1972 | Bailey ........................ 260/240 |
| 3,725,067 A | 4/1973 | Bailey et al. ............... 430/476 |
| 3,926,631 A | 12/1975 | Arai et al. .................. 430/226 |
| 4,128,425 A | 12/1978 | Greenwald .................. 430/440 |
| 4,500,630 A | 2/1985 | Sato et al. .................. 430/386 |
| 4,823,985 A | 4/1989 | Grollier et al. ................. 222/1 |
| 4,865,617 A * | 9/1989 | Junino et al. .................... 8/409 |
| 5,180,396 A | 1/1993 | Grollier et al. ................. 8/405 |
| 5,230,710 A * | 7/1993 | Akram et al. .................... 8/409 |
| 5,256,526 A | 10/1993 | Susuki et al. ............... 430/384 |
| 5,279,620 A * | 1/1994 | Junino et al. .................... 8/409 |
| 5,364,414 A * | 11/1994 | Lang et al. ...................... 8/409 |
| 5,376,146 A | 12/1994 | Casperson et al. ............... 8/408 |
| 5,441,863 A | 8/1995 | Tang et al. ................. 430/558 |
| 5,457,210 A | 10/1995 | Kim et al. ................. 548/262.4 |
| 5,494,490 A * | 2/1996 | Audousset et al. ............... 8/409 |
| 5,578,087 A * | 11/1996 | Audousset et al. ............... 8/409 |
| 5,609,649 A * | 3/1997 | Junino et al. .................... 8/409 |
| 5,690,695 A * | 11/1997 | Cotteret et al. ................. 8/409 |
| 5,769,903 A * | 6/1998 | Audousset et al. ............... 8/409 |
| 5,785,717 A | 7/1998 | Maubru et al. ................. 8/409 |
| 5,980,584 A * | 11/1999 | Lim et al. ...................... 8/408 |
| 6,074,438 A * | 6/2000 | Lim et al. ...................... 8/409 |

FOREIGN PATENT DOCUMENTS

| | | |
|---|---|---|
| DE | 23 59 399 | 6/1975 |
| DE | 38 43 892 | 6/1990 |
| DE | 41 32 615 | 4/1993 |
| DE | 41 33 957 | 4/1993 |
| DE | 195 34 214 | 10/1996 |
| DE | 195 43 988 | 5/1997 |
| DE | 196 37 371 | 3/1998 |
| EP | 0 119 860 | 9/1984 |
| EP | 0 244 160 | 11/1987 |
| EP | 0 285 274 | 10/1988 |
| EP | 0 304 001 | 2/1989 |
| EP | 0 456 226 | 11/1991 |
| EP | 0 488 248 | 6/1992 |
| EP | 0 488 909 | 6/1992 |
| EP | 0 518 238 | 12/1992 |
| EP | 0 557 851 | 9/1993 |
| EP | 0 578 248 | 1/1994 |
| EP | 0 658 339 | 6/1995 |
| EP | 0 728 464 | 8/1996 |
| EP | 0 832 640 | 4/1998 |
| FR | 2 075 583 | 10/1971 |
| FR | 2 586 913 | 3/1987 |
| FR | 2 624 730 | 6/1989 |
| FR | 2 733 749 | 11/1996 |
| FR | 2 750 048 | 12/1997 |
| GB | 1 026 978 | 4/1966 |
| GB | 1 153 196 | 5/1969 |
| GB | 1 458 377 | 12/1976 |
| GB | 2 211 517 | 7/1989 |
| GB | 2 260 135 | 4/1993 |
| JP | 58-42045 | 3/1983 |
| JP | 59-99437 | 6/1984 |
| JP | 59-162548 | 9/1984 |
| JP | 59-171956 | 9/1984 |
| JP | 60-33552 | 2/1985 |
| JP | 60-43659 | 3/1985 |
| JP | 60-172982 | 9/1985 |
| JP | 62-279337 | 12/1987 |
| JP | 2019565 | 1/1990 |
| JP | 6-236011 | 8/1994 |
| JP | 7-36159 | 2/1995 |
| JP | 7-84348 | 3/1995 |
| JP | 7-92632 | 4/1995 |
| JP | 7-98489 | 4/1995 |
| JP | 7-244361 | 9/1995 |
| JP | 7-325375 | 12/1995 |
| WO | WO 94/08969 | 4/1994 |
| WO | WO 94/08970 | 4/1994 |
| WO | WO 96/15765 | 5/1996 |

OTHER PUBLICATIONS

Hans Beyer, Gerhard Wolter und Herbert Lemke : Über die Pyrazolbildung aus α–Chloracetessigester und Thiocarbohydrazid, Chemische Berichte, vol. 89, No. 11, pp. 2550–2555, Aug. 1956.

Joseph Bailey, "Synthesis of 1H–Pyrazolo[3,20c]–s–Triaxoles and Derived Azamethine Dyes", Journal of the Chemical Society, Perkin Transactions I, 18, 1977, pp. 2047–2052 No month available.

(List continued on next page.)

Primary Examiner—Margaret Einsmann
(74) Attorney, Agent, or Firm—Finnegan Henderson Farabow Garrett & Dunner, L.L.P.

(57) ABSTRACT

The invention relates to a composition for the oxidation dyeing of keratin fibres, and in particular human keratin fibres such as the hair, comprising, in a medium which is suitable for dyeing, at least one oxidation base, 1,3-bis(β-hydroxyethyl)amino-2-methylbenzene and/or at least one of the addition salts thereof with an acid as first coupler, and at least one selected heterocyclic coupler as second coupler, as well as to the dyeing process using this composition.

34 Claims, No Drawings

OTHER PUBLICATIONS

Mohamed Helmy Elnagdi et al., "Routes for the Synthesis of 3,5–Diaminopyrazoles, 2–Aminopyrazolo[1,5–a]pyrimidines and 5–Aminopyrazolo[1,5–a]pyrimidines", Journal f. prakt. Chemie. Band 320, Heft 4, 1978, pp. 533–538 No month available.

Thomas Kauffmann et al., "Synthese von Amidrazonen aus Nitrilen und Natriumhydrazid", Chemische Berichte, vol. 97, No. 9, 1964, pp. 3436–3443 No month available.

E. J. Browne et al., "Triazoles. Part VII. Syntheses of Substituted 1,2,4–Triazoles", Journal of the Chemical Society, Dec. 1962, pp. 5149–5152.

Philip Magnus et al., "Synthesis of Helical Polyβ–pyrroles. Multiple Atropisomerism Resulting in Helical Enantiomorphic Conformations", J. Am. Chem. Soc. vol. 112, No. 6, Mar. 14, 1990, pp. 2465–2468.

Von Dr. H. Gold, "Die Reaktion von Cyanurchlorid mit Dimethylformamid", Angew. Chem. vol. 72, No. 24, 1960, pp. 956–959 No month available.

Lidia Wyzgowska et al., "O Reakcjach Trikarboetoksymetanu. VIII", ACTA Poloniae Pharmaceutica, vol. 38, No. 307, 1981, pp. 83–88 No month availabe.

E. Hannig et al., "Zur Kenntnis des 4–aminierten Phenylbutazons", Die Pharmazie, 1980, pp. 231–236 No month available.

Mohamed Helmi Elnagdi et al., "Studies on 3,5–pyrazolidinediones. IV. Addition of 4–Arylazo–3,5–pyrazolidinediones to Ethyl Acrylate", Bulletin of the Chemical Society of Japan, vol. 46, No. 6, 1973, pp. 1830–1833 No month available.

Giuliana Gardillo et al., "Sulle 1,2–difenil–3,5–dichetopirazolidine—Prodotti di reazione con biossido di azoto", Gazzette Chimica Italiana, vol. 96, 1966, pp. 973–985 No month available.

Victor Israel Cohen, "A New Method of Synthesis of Some 2–Aryl and 2–Heterocyclic Benzimidazole, Benzoxazole and Benzothiazole Derivatives", Journal of Heterocyclic Chemistry, vol. 16, No. 1, Jan. 1979, pp. 13–16.

Mohamed I. Ali et al., "Reactions with Thiazolo[3,2–b] –s–triazol–3(2H)–ones", Journal f. prakt. Chemie, Bank 318, Heft 1, 1976, pp. 12–18 No month available.

S. Syed Shafi et al., "Studies on Biologically Active Heterocycles Part I. Synthesis and Antibacterial Activity of Some 2,5–Disubstituted–1,3,4–Oxadiazole, 1,3,4–Thiadiazole, 1,2,4–Triazole, and 4–Thiazolidinone", Indian Journal of Heterocyclic Chemistry, vol. 5, Oct.–Dec. 1995, pp. 135–138.

Eser Ilhan et al., "Synthese von 6–Benzyliden–2–(α, α–diphenyl–α–hydroxyacetyl)–thiazolo[3,2–b] –s–triazol–5–onen als potentiell biologish wirksame Stoffe", Archiv der Pharmazie, vol. 327, No. 12, Dec. 1994, pp. 825–826.

Ferenc Korodi et al., "Fused 1,4,5–Triazole Heterocycles. III. Syntheses and Structures of Novel [1,2,4]triazolo[1,3] thiazinoquinolinest", Heterocyclic Communications, vol. 1, No. 4, 1995, pp. 297–306 No month available.

Henryk Foks et al., "Synthesis and Biological Activity of Thiazolo–1,2–4–Triazoles", Acta Poloniae Pharmaceutica, vol. 52, No. 5, Sep./Oct. 1995, pp. 415–520.

English language Derwent Abstract of DE 23 59 399, Jun. 1975.

English language Derwent Abstract of DE 38 43 892, Jun. 1990.

English language Derwent Abstract of DE 41 32 615, Apr. 1993.

English language Derwent Abstract of DE 41 33 957, Apr. 1993.

English language Derwent Abstract of DE 195 34 214, Oct. 1996.

English language Derwent Abstract of DE 195 43 988, May 1997.

English language Derwent Abstract of DE 196 37 371, Mar. 1998.

English language abstract of EP 0 488 909, Jun. 1992.

English language Derwent Abstract of EP 0 832 640, Apr. 1998.

English language Derwent Abstract FR 2 733 749, Nov. 1996.

English language Derwent Abstract FR 2 750 048, Dec. 1997.

English language Derwent Abstract JP 58–42045, Mar. 1983.

English language Derwent Abstract JP 59–99437, Jun. 1984.

English language Derwent Abstract of JP 59–162548, Sep. 1984.

English language Derwent Abstract of JP 49–171956, Sep. 1984.

English language Derwent Abstract of JP 60–33552, Feb. 1985.

English language Derwent Abstract of JP 60–43659, Mar. 1985.

English language Derwent Abstract of JP 60–172982, Sep. 1985.

English language Derwent Abstract of JP 62–279337, Dec. 1987.

English language Derwent Abstract of JP 6–236011, Aug. 1994.

English language Derwent Abstract of JP 7–36159, Feb. 1995.

English language Derwent Abstract of JP 7–84348, Mar. 1995.

English language Derwent Abstract of JP 7–92632, Apr. 1995.

English language Derwent Abstract of JP 7–98489, Apr. 1995.

English language Derwent Abstract of JP 7–244361, Sep. 1995.

English language Derwent Abstract of JP 7–325375, Dec. 1995.

Paul Carter et al., "Studies on the Synthesis of Antitumor Agent CC–1065. Synthesis of PDE I and PDE II, Inhibitors of cyclic Adenosine–3',5'–monophosphiate Phosphodiesterase Using the 3,3'–Bipyrrole Strategy", J. Am. Chem. Soc., 1987, 109, pp. 2711–2717.

H. Koopman, "Investigations on Herbicides IV", Recueil, vol. 80, No. 9–10, Sep.–Oct. 1961, pp. 1075–1083.

S.A. Hiller et al., "Electron Density Distribution in Heterocyclic Systems With Two Adjacent Nitrogen Atoms", Chemistry of Heterocyclic Compounds, vol. 3, No. 1, Jan.–Feb. 1967, pp. 93–96.

R. Stollé, "Ueber die Ueberführung der secundären Säurehydrazide in Derivate des Furodiazols, Pyrrodiazols und Thiodiazols", Berichte der Deutschen Chemischen Gesellschaft, 1899, pp. 797–798.

* cited by examiner

COMPOSITION FOR THE OXIDATION DYEING OF KERATIN FIBERS AND DYEING PROCESS USING THIS COMPOSITION

The invention relates to a composition for the oxidation dyeing of keratin fibres, and in particular human keratin fibres such as the hair, comprising, in a medium which is suitable for dyeing, at least one oxidation base, 1,3-bis(β-hydroxyethyl)amino-2-methylbenzene and/or at least one of the addition salts thereof with an acid as first coupler, and at least one selected heterocyclic coupler as second coupler, as well as to the dyeing process using this composition.

It is known practice to dye keratin fibres, and in particular human hair, with dye compositions containing oxidation dye precursors, in particular ortho- or para-phenylenediamines, ortho- or para-aminophenols and heterocyclic bases, which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers allows a wide range of colours to be obtained.

The so-called "permanent" coloration obtained by means of these oxidation dyes must moreover satisfy a certain number of requirements. Thus, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible coloration differences along the same length of keratin fibre, which may in fact be differently sensitized (i.e. damaged) between its tip and its root.

Compositions for the oxidation dyeing of keratin fibres containing one or more oxygen bases, one or more 2,6-diaminotoluene derivatives as second coupler, and optionally one or more additional couplers chosen from the couplers conventionally used in the field of oxidation dyeing, such as resorcinol and derivatives thereof, naphthalene derivatives or pyridine derivatives, have already been proposed, in particular in patent applications DE-A-4,132,615 and DE-A-19,637,371. However, although the colorations obtained using such compositions are highly chromatic, they are not entirely satisfactory, in particular as regards their fastness with respect to the various treatments and natural attacking factors to which keratin fibres may be subjected.

The Applicant has now discovered that it is possible to obtain novel dyes which are capable of giving intense and highly chromatic colorations, and which show good resistance to the various attacking factors to which the fibres may be subjected, by combining at least one oxidation base, 1,3-bis(β-hydroxyethyl)amino-2-methylbenzene and/or at least one of the addition salts thereof with an acid as first coupler, and at least one suitably selected heterocyclic coupler as second coupler.

This discovery forms the basis of the present invention.

A first subject of the invention is thus a composition for the oxidation dyeing of keratin fibres, and in particular human keratin fibres such as the hair, characterized in that it comprises, in a medium which is suitable for dyeing:
- at least one oxidation base,
- 1,3-bis(β-hydroxyethyl)amino-2-methylbenzene and/or at least one of the addition salts thereof with an acid, as first coupler; and
- at least one heterocyclic coupler, as second coupler;

it being understood that when the dye composition contains a pyrimidine oxidation base and/or 2-β-hydroxyethyl-para-phenylenediamine and/or one of the addition salts thereof with an acid, then the heterocyclic coupler is other than a pyridine coupler.

The dye composition in accordance with the invention gives intense, highly chromatic colorations which show excellent resistance properties with respect both to atmospheric agents such as light and bad weather, and to perspiration and the various treatments to which the hair may be subjected.

A subject of the invention is also a process for the oxidation dyeing of keratin fibres using this dye composition.

Among the heterocyclic couplers which can be used as second couplers in the dye composition according to the invention, mention may be made in particular of indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives and pyridine derivatives, and the addition salts thereof with an acid.

Among the indole derivatives which can be used as heterocyclic couplers in the dye composition in accordance with the invention, mention may be made more particularly of the compounds of formula (I) below, and the addition salts thereof with an acid:

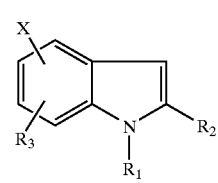

(I)

in which:
$R_1$ represents a hydrogen atom, a $C_1$–$C_4$ alkyl radical, a $C_2$–$C_4$ mono- or polyhydroxyalkyl radical or a $C_1$–$C_4$ aminoalkyl radical in which the amine is mono- or disubstituted with a $C_1$–$C_4$ alkyl group;
$R_2$ represents a hydrogen atom or a $C_1$–$C_4$ alkyl radical;
$R_3$ represents a hydrogen atom or a $C_1$–$C_4$ alkyl or hydroxyl radical;
X represents a hydroxyl radical or a radical $NHR_4$ in which $R_4$ represents a hydrogen atom or a $C_1$–$C_4$ alkyl or $C_1$–$C_4$ hydroxyalkyl radical.

Among the indole derivatives of formula (I) above, mention may be made more particularly of 4-hydroxyindole, 6-hydroxyindole, 7-aminoindole, 6-aminoindole, 7-hydroxyindole, 7-ethyl-6-(β-hydroxyethyl)aminoindole, 4-aminoindole, 6-hydroxy-1-methylindole, 5,6-dihydroxyindole, 4-hydroxy-1-N-methylindole, 4-hydroxy-2-methylindole, 4-hydroxy-5-methylindole, 4-hydroxy-1-N-(β-hydroxyethyl)indole, 4-hydroxy-1 -N-(β- hydroxypropyl) indole, 1-N-(β,γ-dihydroxypropyl)-4-hydroxyindole, 4-hydroxy-1-N-(β-hydroxyethyl)-5-methylindole and 1-N-(g-dimethylaminopropyl)4-hydroxyindole, and the addition salts thereof with an acid.

Among the indoline derivatives which can be used as heterocyclic couplers in the dye composition in accordance with the invention, mention may be made in particular of 4-hydroxyindoline, 6-hydroxyindoline, 6-aminoindoline and 5,6-dihydroxyindoline, and the addition salts thereof with an acid.

Among the benzimidazole derivatives which can be used as heterocyclic couplers in the dye composition in accordance with the invention, mention may be made more particularly of the compounds of formula (II) below, and the addition salts thereof with an acid:

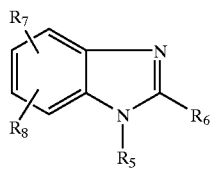

(II)

in which:
$R_5$ represents a hydrogen atom or a $C_1$–$C_4$ alkyl radical,
$R_6$ represents a hydrogen atom or a $C_1$–$C_4$ alkyl or phenyl radical, $R_7$ represents a hydroxyl, amino or methoxy radical,
$R_8$ represents a hydrogen atom or a hydroxyl, methoxy or $C_1$–$C_4$ alkyl radical;
with the proviso that:
when $R_7$ denotes an amino radical, then it occupies position 4,
when $R_7$ occupies position 4, then $R_8$ occupies position 7,
when $R_7$ occupies position 5, then $R_8$ occupies position 6.

Among the benzimidazole derivatives of formula (II) above, mention may be made more particularly of 4-hydroxybenzimidazole, 4-aminobenzimidazole, 4-hydroxy-7-methylbenzimidazole, 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxy-benzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole and 5,6-dimethoxybenzimidazole, and the addition salts thereof with an acid.

Among the benzomorpholine derivatives which can be used as heterocyclic couplers in the dye composition in accordance with the invention, mention may be made more particularly of the compounds of formula (III) below, and the addition salts thereof with an acid:

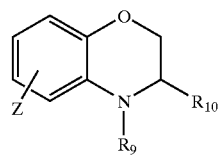

(III)

in which:

$R_9$ and $R_{10}$, which may be identical or different, represent a hydrogen atom or a $C_1$–$C_4$ alkyl radical,
Z represents a hydroxyl or amino radical.

Among the benzomorpholine derivatives of formula (III) above, mention may be made more particularly of 6-hydroxy-1,4-benzomorpholine, N-methyl-6-hydroxy-1,4-benzomorpholine and 6-amino-1,4-benzomorpholine, and the addition salts thereof with an acid.

Among the sesamol derivatives which can be used as heterocyclic couplers in the dye composition in accordance with the invention, mention may be made more particularly of the compounds of formula (IV) below, and the addition salts thereof with an acid:

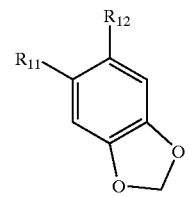

(IV)

in which:
$R_{11}$ denotes a hydroxyl, amino, $(C_1$–$C_4)$alkylamino, monohydroxy$(C_1$–$C_4)$alkylamino or polyhydroxy $(C_2$–$C_4)$alkylamino radical,
$R_{12}$ denotes a hydrogen or halogen atom or a $C_1$–$C_4$ alkoxy radical.

Among the sesamol derivatives of formula (IV) above, mention may be made more particularly of 2-bromo-4,5-methylenedioxyphenol, 2-methoxy-4,5-methylenedioxyaniline and 2-(b-hydroxyethyl)amino-4,5-methylenedioxybenzene, and the addition salts thereof with an acid.

Among the pyrazoloazole derivatives which can be used as heterocyclic couplers in the dye composition in accordance with the invention, mention may be made more particularly of the compounds described in the following patents and patent applications: FR 2,075,583, EP-A-119,860, EP-A-285,274, EP-A-244,160, EP-A-578,248, GB 1,458,377, U.S. Pat. No. 3,227,554, U.S. Pat. No. 3,419,391, U.S. Pat. No. 3,061,432, U.S. Pat. No. 4,500,630, U.S. Pat. No. 3,725,067, U.S. Pat. No. 3,926,631, U.S. Pat. No. 5,457,210, JP 84/99437, JP 83/42045, JP 84/162548, JP 84/171956, JP 85/33552, JP 85/43659, JP 85/172982, JP 85/190779 and in the following publications: Chem. Ber. 32, 797 (1899), Chem. Ber. 89, 2550, (1956), J. Chem. Soc. Perkin trans 1, 2047, (1977), J. Prakt. Chem., 320, 533, (1978); the teachings of which form an integral part of the present application.

As pyrazoloazole derivatives, mention may be made most particularly of:
2-methylpyrazolo[1,5-b]-1,2,4-triazole,
2-ethylpyrazolo[1,5-b]-1,2,4-triazole,
2-isopropylpyrazolo[1,5-b]-1,2,4-triazole,
2-phenylpyrazolo[1,5-b]-1,2,4-triazole,
2,6-dimethylpyrazolo[1,5-b]-1,2,4-triazole,
7-chloro-2,6-dimethylpyrazolo[1,5-b]-1,2,4-triazole,
3,6-dimethylpyrazolo[3,2-c]-1,2,4-triazole,
6-phenyl-3-methylthiopyrazolo[3,2-c]-1,2,4-triazole and
6-aminopyrazolo[1,5-a]benzimidazole,
and the addition salts thereof with an acid.

Among the pyrroloazole derivatives which can be used as heterocyclic couplers in the dye composition in accordance with the invention, mention may be made more particularly of the compounds described in the following patents and patent applications: U.S. Pat. No. 5,256,526, EP-A-557,851, EP-A-578,248, EP-A-518,238, EP-A-456,226, EP-A-488,909, EP-A-488,248, and in the following publications:

D. R. Liljegren Ber. 1964, 3436;

E. J. Browne, J. C. S., 1962, 5149;

P. Magnus, J. A. C. S., 1990, 112, 2465;

P. Magnus, J. A. C. S., 1987, 109, 2711; Angew. Chem. 1960, 72, 956;

and Rec. Trav. Chim. 1961, 80, 1075; the teachings of which form an integral part of the present application.

As pyrroloazole derivatives, mention may be made most particularly of:

5-cyano-4-ethoxycarbonyl-8-methylpyrrolo[1,2-b]-1,2,4-triazole, 5-cyano-8-methyl-4-phenylpyrrolo[1,2-b]-1,2,4-triazole, 7-amido-6-ethoxycarbonylpyrrolo[1,2-a]benzimidazole, and the addition salts thereof with an acid.

Among the imidazoloazole derivatives which can be used as heterocyclic couplers in the dye composition in accordance with the invention, mention may be made more particularly of the compounds described in the following patents and patent applications: U.S. Pat. No. 5,441,863; JP 62-279,337; JP 06-236,011 and JP 07-092,632, the teachings of which form an integral part of the present application.

As imidazoloazole derivatives, mention may be made most particularly of:

7,8-dicyanoimidazolo[3,2-a]imidazole, 7,8-dicyano-4-methylimidazolo[3,2-a]imidazole, and the addition salts thereof with an acid.

Among the pyrazolopyrimidine derivatives which can be used as heterocyclic couplers in the dye composition in accordance with the invention, mention may be made more particularly of the compounds described in the following patent application: EP-A-304,001, the teaching of which forms an integral part of the present application.

As pyrazolopyrimidine derivatives, mention may be made most particularly of:

pyrazolo[1,5-a]pyrimidin-7-one, 2,5-dimethylpyrazolo[1,5-a]pyrimidin-7-one, 2-methyl-6-ethoxycarbonylpyrazolo[1,5-a]pyrimidin-7-one, 2-methyl-5-methoxymethylpyrazolo[1,5-a]pyrimidin-7-one, 2-tert-butyl-5-trifluoromethylpyrazolo[1,5-a]pyrimidin-7-one, 2,7-dimethylpyrazolo[1,5-a]pyrimidin-5-one, and the addition salts thereof with an acid.

Among the pyrazoline-3,5-dione derivatives which can be used as heterocyclic couplers in the dye composition in accordance with the invention, mention may be made more particularly of the compounds described in the following patents and patent applications: JP 07-036159, JP 07-084348 and U.S. Pat. No. 4,128,425, and in the following publications:

L. WYZGOWSKA, Acta. Pol. Pharm. 1982, 39 (1–3), 83

E. HANNIG, Pharmazie, 1980, 35 (4), 231

M. H. ELNAGDI, Bull. Chem. Soc. Jap., 46 (6), 1830, 1973

G. CARDILLO, Gazz. Chim. Ital. 1966, 96, (8–9), 973, the teachings of which form an integral part of the present application.

As pyrazoline-3,5-dione derivatives, mention may be made most particularly of:

1,2-diphenylpyrazoline-3,5-dione, 1,2-diethylpyrazoline-3,5-dione, and the addition salts thereof with an acid.

Among the pyrrolo[3,2-d]oxazole derivatives which can be used as heterocyclic couplers in the dye composition in accordance with the invention, mention may be made more particularly of the compounds described in patent application JP 07-325,375, the teaching of which forms an integral part of the present application.

Among the pyrazolo[3,4-d]thiazole derivatives which can be used as heterocyclic couplers in the dye composition in accordance with the invention, mention may be made more particularly of the compounds described in patent application JP 07-244,361 and in J. Heterocycl. Chem. 16, 13, (1979).

Among the thiazoloazole S-oxide and thiazoloazole S,S-dioxide derivatives which can be used as heterocyclic couplers in the dye composition in accordance with the invention, mention may be made more particularly of the compounds described in the following documents:

JP 07-098489;

Khim. Geterotsilk. Soedin, 1967, p. 93;

J. Prakt. Chem., 318, 1976, p. 12;

Indian J. Heterocycl. Chem. 1995, 5, (2), p. 135;

Acta. Pol. Pharm. 1995, 52 (5), 415;

Heterocycl. Commun. 1995, 1 (4), 297;

Arch. Pharm. (Weinheim, Ger.), 1994, 327 (12), 825.

As indicated above, when the dye composition in accordance with the invention contains neither pyrimidine oxidation base nor 2-β-hydroxyethyl-para-phenylenediamine or one of the addition salts thereof with an acid, then the heterocyclic coupler(s) can also be chosen from pyridine couplers.

Among the pyridine couplers which can be used in the dye composition in accordance with the invention, mention may be made in particular of 3-(3',5'-diamino-2'-pyridyloxy)-2-hydroxypropanol, the pyridine derivatives of formula (V) below, and the addition salts thereof with an acid:

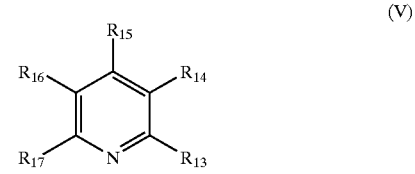

(V)

in which:

$R_{13}$ represents a hydrogen atom or a hydroxyl, amino or —$OCH_2CH_2COCH_2CH_2OH$ radical, $R_{14}$ and $R_{16}$, which may be identical or different, represent a hydrogen atom or a hydroxyl, amino or $C_1$–$C_4$ alkyl radical, $R_{15}$ represents a hydrogen atom or a $C_1$–$C_4$ alkyl radical, $R_{17}$ represents a hydrogen atom or a hydroxyl or amino radical;

it being understood that these compounds of formula (V) do not comprise more than two (substituted or unsubstituted) amino groups or not more than two hydroxyl groups or not more than one amino group and one hydroxyl group per molecule, these amino and/or hydroxyl groups necessarily being in a meta position relative to each other.

Among the pyridine derivatives of formula (V) above which may be mentioned more particularly are 2,6- dihydroxy-4-methylpyridine, 2,6-dihydroxy-3,4-dimethylpyridine, 2,6-diaminopyridine, 3-oxo-5-(3',5'-diamino-2'-pyridyloxy)pentanol and 3-(3',5'-diamino-2'-pyridyloxy)-2-hydroxypropanol, and the addition salts thereof with an acid.

The nature of the oxidation base(s) used in the dye composition in accordance with the invention is not critical. They can be chosen in particular from para-phenylenediamines, double bases, para-aminophenols, ortho-aminophenols and heterocyclic oxidation bases.

Among the para-phenylenediamines which can be used as oxidation base in the dye compositions in accordance with the invention, mention may be made in particular of the compounds of formula (VI) below, and the addition salts thereof with an acid:

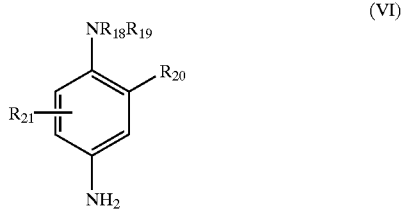

(VI)

in which:
R$_{18}$ represents a hydrogen atom, a C$_1$–C$_4$ alkyl radical, C$_1$–C$_4$ monohydroxyalkyl radical, C$_2$–C$_4$ polyhydroxyalkyl radical, (C$_1$–C$_4$)alkoxy(C$_1$–C$_4$)alkyl radical or a C$_1$–C$_4$ alkyl radical substituted with a nitrogenous, phenyl or 4'-aminophenyl group;

R$_{19}$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical or a C$_1$–C$_4$ alkyl radical substituted with a nitrogenous group;

R$_{20}$ represents a hydrogen atom, a halogen atom such as a chlorine, bromine, iodine or fluorine atom, a C$_1$–C$_4$ alkyl radical, a C$_1$–C$_4$ monohydroxyalkyl radical, a C$_1$–C$_4$ hydroxyalkoxy radical, a C$_1$–C$_4$ acetylaminoalkoxy radical, a C$_1$–C$_4$ mesylaminoalkoxy radical or a C$_1$–C$_4$ carbamoylaminoalkoxy radical, R$_{21}$ represents a hydrogen or halogen atom or a C$_1$–C$_4$ alkyl radical.

Among the nitrogenous groups of formula (VI) above which may be mentioned in particular are amino, mono (C$_1$–C$_4$)alkylamino, di(C$_1$–C$_4$)alkylamino, tri(C$_1$–C$_4$) alkylamino, monohydroxy(C$_1$–C$_4$)alkylamino, imidazolinium and ammonium radicals.

Among the para-phenylenediamines of formula (VI) above, mention may be made more particularly of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxy-ethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines of formula (VI) above which are most particularly preferred are para-phenylenediamine, para-tolylenediamine, 2-isoproyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

According to the invention, the expression "double bases" means compounds comprising at least two aromatic nuclei bearing amino and/or hydroxyl groups.

Among the double bases which can be used as oxidation bases in the dye compositions in accordance with the invention, mention may be made in particular of the compounds corresponding to formula (VII) below, and the addition salts thereof with an acid:

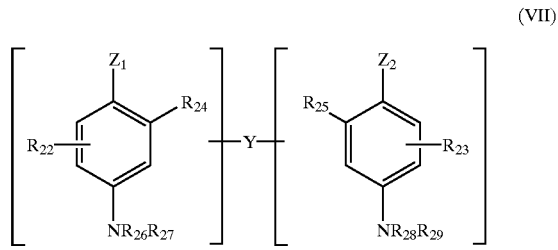

(VII)

in which:
Z$_1$ and Z$_2$, which may be identical or different, represent a hydroxyl or —NH$_2$ radical which can be substituted with a C$_1$–C$_4$ alkyl radical or with a linker arm Y;

the linker arm Y represents a linear or branched alkylene chain comprising from 1 to 14 carbon atoms which can be interrupted or terminated with one or more nitrogenous groups and/or with one or more hetero atoms such as oxygen, sulphur or nitrogen atoms, and optionally substituted with one or more hydroxyl or C$_1$–C$_6$ alkoxy radicals;

R$_{22}$ and R$_{23}$ represent a hydrogen or halogen atom, a C$_1$–C$_4$ alkyl radical, a C$_1$–C$_4$ monohydroxyalkyl radical, a C$_2$–C$_4$ polyhydroxyalkyl radical, a C$_1$–C$_4$ aminoalkyl radical or a linker arm Y;

R$_{24}$, R$_{25}$, R$_{26}$, R$_{27}$, R$_{28}$ and R$_{29}$, which may be identical or different, represent a hydrogen atom, a linker arm Y or a C$_1$–C$_4$ alkyl radical;

it being understood that the compounds of formula (VII) comprise only one linker arm Y per molecule.

Among the nitrogenous groups of formula (VII) above which may be mentioned in particular are amino, mono (C$_1$–C$_4$)alkylamino, di(C$_1$–C$_4$)alkylamino, tri(C$_1$–C$_4$) alkylamino, monohydroxy(C$_1$–C$_4$)alkylamino, imidazolinium and ammonium radicals.

Among the double bases of formula (VII) above which may be mentioned more particularly are N,N'-bis(β-hydroxyethyl)-N,N'-bis(4'-aminophenyl)-1,3-diaminopropanol, N,N'-bis(β-hydroxyethyl)-N,N'-bis( 4'-aminophenyl)ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4'-methylaminophenyl)tetra-methylenediamine, N,N'-bis (ethyl)-N,N'-bis(4'-amino-3'-methylphenyl)ethylenediamine and 1,8-bis(2,5-diaminophenoxy)-3,5-dioxaoctane, and the addition salts thereof with an acid.

Among these double bases of formula (VII), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

Among the para-aminophenols which can be used as oxidation bases in the dye compositions in accordance with the invention, mention may be made in particular of the compounds of formula (VIII) below, and the addition salts thereof with an acid:

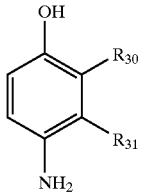

(VIII)

in which:
R$_{30}$ represents a hydrogen or halogen atom, a C$_1$–C$_4$ alkyl radical, a C$_1$–C$_4$ monohydroxyalkyl radical, a (C$_1$–C$_4$) alkoxy(C$_1$–C$_4$)alkyl radical, a C$_1$–C$_4$ aminoalkyl radical or a hydroxy(C$_1$–C$_4$)alkylamino(C$_1$–C$_4$)alkyl radical, R$_{31}$ represents a hydrogen or halogen atom, a C$_1$–C$_4$ alkyl radical, a C$_1$–C$_4$ monohydroxyalkyl radical, a C$_2$–C$_4$ polyhydroxyalkyl radical, a C$_1$–C$_4$-aminoalkyl radical, a cyano(C$_1$–C$_4$)alkyl radical or a (C$_1$–C$_4$)alkoxy (C$_1$–C$_4$)alkyl radical, it being understood that at least one of the radicals R$_{30}$ and R$_{31}$ represents a hydrogen atom.

Among the para-aminophenols of formula (VIII) above which may be mentioned more particularly are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be used as oxidation bases in the dye compositions in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as oxidation bases in the dye compositions in accordance with the invention, mention may be made more particularly of pyridine derivatives, pyrimidine derivatives and pyrazole derivatives, and the addition salts thereof with an acid.

Among the pyridine derivatives which may be mentioned more particularly are the compounds described, for example, in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, as well as pyrazolopyrimidine derivatives such as those mentioned in patent application FR-A-2,750,048 and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a] pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a] pyrimidine-3,7-diamine and 2,5-N-7,N-7-tetramethylpyrazolo[1,5-a]pyrimidine-3,7-diamine, and the addition salts thereof and the tautomers thereof, when a tautomeric equilibrium exists, and the addition salts thereof with an acid.

Among the pyrazole derivatives, mention may be made more particularly of the compounds described in patents or patent applications DE 3,843,892, DE 4,133,957, WO 94/08969, WO 94/08970, FR-A-2,733,749 and DE 195 43 988 such as 4,5-diamino-1-methylpyrazole, 3,4-diaminopyrazole, 4,5-diamino-1-(4'chlorobenzyl)pyrazole, 4,5-diamino-1,3-dimethyl pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(b-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the addition salts thereof with an acid.

The oxidation base(s) preferably represent(s) from 0.0005 to 12% by weight approximately relative to the total weight of the dye composition in accordance with the invention, and even more preferably from 0.005 to 6% by weight approximately relative to this weight.

The 1,3-bis(β-hydroxyethyl)amino-2-methylbenzene and/or the addition salt(s) thereof with an acid, which are used as first coupler according to the invention, preferably represent(s) from 0.001 to 10% by weight approximately relative to the total weight of the dye composition and even more preferably from 0.01 to 5% by weight approximately relative to this weight.

The heterocyclic coupler(s) preferably represent(s) from 0.0001 to 10% by weight approximately relative to the total weight of the dye composition in accordance with the invention, and even more preferably from 0.005 to 5% by weight approximately relative to this weight.

The dye composition in accordance with the invention can also contain one or more additional couplers other than 1,3-bis(β-hydroxyethyl)amino-2-methylbenzene, heterocyclic couplers in accordance with the invention and addition salts thereof with an acid and/or one or more direct dyes, in particular to modify the shades or to enrich them with glints.

Among the couplers which can additionally be present in the dye composition in accordance with the invention, mention may be made in particular of benzenic couplers such as, for example, meta-aminophenols, meta-phenylenediamines and meta-diphenols, and the addition salts thereof with an acid.

When they are present, these additional couplers preferably represent from 0.0001 to 10% by weight approximately relative to the total weight of the dye composition, and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for dyeing (or support) for the dye composition in accordance with the invention generally consists of water or a mixture of water and at least one organic solvent to dissolve the compounds which would not be sufficiently soluble in water. Organic solvents which may be mentioned, for example, are $C_1$–$C_4$ alkanols, such as ethanol and isopropanol.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately and can be between 5 and 12 approximately. It can be adjusted to the desired value using acidifying or basifying agents usually used for dyeing keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which may be mentioned, for example, are aqueous ammonia, alkaline carbonates, alkanolamines such as mono-, di- and triethanolamine, 2-methyl-2-aminopropanol and derivatives thereof, sodium hydroxide, potassium hydroxide and the compounds of formula (IX) below:

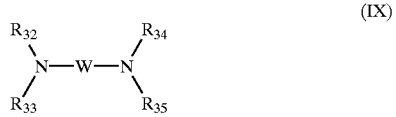

(IX)

in which W is a propylene residue optionally substituted with a hydroxyl group or a $C_1$–$C_4$ alkyl radical; $R_{32}$, $R_{33}$, $R_{34}$ and $R_{35}$, which may be identical or different, represent a hydrogen atom or a $C_1$–$C_4$ alkyl or $C_1$–$C_4$ hydroxyalkyl radical.

The dye composition in accordance with the invention can also contain various adjuvants conventionally used in compositions for dyeing the hair.

Needless to say, a person skilled in the art will take care to select this or these optional additional compounds such that the advantageous properties intrinsically associated with the dye composition in accordance with the invention are not, or are not substantially, adversely affected by the addition(s) envisaged.

The dye composition in accordance with the invention can be in various forms, such as in the form of liquids, creams or gels, which are optionally pressurized, or in any other form which is suitable for dyeing keratin fibres, and in particular human hair.

A subject of the invention is also a process for dyeing keratin fibres, and in particular human keratin fibres such as the hair, using the dye composition as defined above.

According to this process, the dye composition as defined above is applied to the fibres, the colour being developed at acidic, neutral or alkaline pH using an oxidizing agent which is added to the dye composition just at the time of use, or which is present in an oxidizing composition that is applied simultaneously or sequentially in a separate manner.

According to one particularly preferred embodiment of the dyeing process according to the invention, the dye composition described above is mixed, at the time of use, with an oxidizing composition comprising, in a medium which is suitable for dyeing, at least one oxidizing agent which is present in an amount which is sufficient to develop a coloration. The mixture obtained is then applied to the keratin fibres and is left to stand for 3 to 50 minutes approximately, preferably 5 to 30 minutes approximately, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates, persalts such as perborates and persulphates, peracids, enzymes such as 2-electron oxidoreductases, peroxidases and lactases. Hydrogen peroxide is particularly preferred.

The pH of the oxidizing composition containing the oxidizing agent as defined above is such that, after mixing with the dye composition, the pH of the resulting composition applied to the keratin fibres preferably ranges between 3 and 12 approximately and even more preferably between 5 and 11. It is adjusted to the desired value using acidifying or basifying agents usually used for dyeing keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels, or in any other form which is suitable for dyeing keratin fibres, and in particular human hair.

Another subject of the invention is a multi-compartment dyeing device or multi-compartment dyeing "kit" or any other multi-compartment packaging system, a first compartment of which contains the dye composition as defined above and a second compartment of which contains the oxidizing composition as defined above. These devices can be equipped with a means for applying the desired mixture to the hair, such as the devices described in patent FR-2,586,913 in the name of the Applicant.

The examples which follow are intended to illustrate the invention without thereby limiting its scope.

EXAMPLES

Examples 1 to 3 of Dyeing in Alkaline Medium

The dye compositions below in accordance with the invention were prepared (contents in grams):

| EXAMPLE | 1 | 2 | 3 |
|---|---|---|---|
| para-Phenylenediamine (oxidation base) | 0.22 | — | — |
| para-Aminophenol (oxidation base) | — | 0.44 | — |
| Pyrazolo[1,5-a]pyrimidine-3,7-diamine dihydrochloride (oxidation base) | — | — | 0.88 |
| 1,3-Bis(b-hydroxyethyl)amino-2-methylbenzene (first coupler) | 0.21 | 0.21 | 0.21 |
| 3,6-Dimethylpyrazolo[3,2-c]-1,2,4-triazole (second coupler) | 0.14 | — | — |
| 4-Hydroxyindole (second coupler) | — | 0.26 | — |
| 6-Hydroxy-1,4-benzomorpholine (second coupler) | — | — | 0.30 |
| Common dye support | (*) | (*) | (*) |
| Demineralized water q.s. | 100 g | 100 g | 100 g |

(*): Common dye support No. 1:

| | |
|---|---|
| 96° ethanol | 18 g |
| Sodium metabisulphite as an aqueous 35% solution | 0.68 g |
| Pentasodium salt of diethylenetriamine pentaacetic acid | 1.1 g |
| Aqueous ammonia containing 20% $NH_3$ | 10 g |

At the time of use, each of the dye compositions described above was mixed with an equivalent amount by weight of 20-volumes hydrogen peroxide (6% by weight) having a pH of about 3.

Each resulting mixture had a pH of about 10±0.2 and was applied for 30 minutes to locks of permanent-waved grey hair containing 90% white hairs.

The hair was then rinsed with water, washed with a standard shampoo, rinsed again and then dried.

The hair was dyed in the shades given in the table below:

| EXAMPLE | SHADE OBTAINED |
|---|---|
| 1 | Iridescent dark purple |
| 2 | Mahogany red |
| 3 | Iridescent ash |

Example 4 of Dyeing in Acidic Medium

The dye composition below in accordance with the invention was prepared:

| | |
|---|---|
| N,N-Bis(β-hydroxyethyl)-para-phenylenediamine sulphate (oxidation base) | 0.63 g |
| 1,3-Bis(β-hydroxyethyl)amino-2-methylbenzene (first coupler) | 0.21 g |
| 2,6-Dihydroxy-3,4-dimethylpyridine (second coupler) | 0.14 g |
| 96° ethanol | 18 g |
| Sodium metabisulphite as an aqueous 35% solution | 0.68 g |
| Pentasodium salt of diethylenetriamine-pentaacetic acid | 1.1 g |
| $K_2HPO_4/KH_2PO_4$ (1.5M/1M) buffer | 10 g |
| Demineralized water q.s. | 100 g |

At the time of use, the dye composition described above was mixed with an equivalent amount by weight of 20-volumes hydrogen peroxide (6% by weight) having a pH of about 3.

The resulting mixture had a pH of about 6.8±0.2, and was applied for 30 minutes to locks of permanent-waved grey hair containing 90% white hairs.

The hair was then rinsed with water, washed with a standard shampoo, rinsed again and then dried.

The hair was dyed in a dark purple-ash shade.

What is claimed is:

1. A composition for the oxidation dyeing of keratin fibres comprising, in a medium which is suitable for dyeing:

(a) at least one oxidation base, and
   (b) at least two couplers, wherein
      the first coupler is chosen from 1,3-bis(2-hydroxyethyl)amino-2-methylbenzene and an addition salt thereof with an acid; and
      the second coupler is chosen from a heterocyclic coupler chosen from indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo(2,3-d)oxazole derivatives, pyrazolo(3,4-d)thiazole derivatives, thiazoloazole S-oxide derivatives, thiazoloazole S,S-dioxide derivatives, pyridine derivatives and the addition salts thereof with an acid,
      provided that if said dye composition contains at least one oxidation base chosen from a pyrimidine base, 2-β-hydroxyethyl-para-phenylenediamine, and an addition salt thereof with an acid, then the heterocyclic coupler is other than a pyridine coupler.

2. The composition according to claim 1, wherein the keratin fibres are human keratin fibres.

3. The composition according to claim 1, wherein the indole derivatives are chosen from compounds corresponding to formula (I), and the addition salts thereof with an acid:

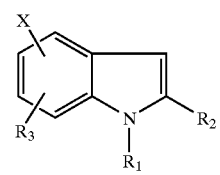

(I)

in which:
   $R_1$ is chosen from hydrogen, $C_1$–$C_4$ alkyl radicals, $C_2$–$C_4$ monohydroxyalkyl radicals, $C_2$–$C_4$ or polyhydroxyalkyl radicals, and $C_1$–$C_4$ aminoalkyl radicals in which the amine is mono- or disubstituted with a $C_1$–$C_4$ alkyl group;
   $R_2$ is chosen from hydrogen and $C_1$–$C_4$ alkyl radicals;
   $R_3$ is chosen from hydrogen, $C_1$–$C_4$ alkyl radicals, and a hydroxyl radical;
   X is chosen from a hydroxyl radical and an $NHR_4$ radical, wherein $R_4$ is chosen from hydrogen, $C_1$–$C_4$ alkyl radicals, and $C_1$–$C_4$ hydroxyalkyl radicals.

4. The composition according to claim 3, wherein the indole derivatives of formula (I) are chosen from 4-hydroxyindole, 6-hydroxyindole, 7-aminoindole, 6-aminoindole, 7-hydroxyindole, 7-ethyl-6-(β-hydroxyethyl)aminoindole, 4-aminoindole, 6-hydroxy-1-methylindole, 5,6-dihydroxyindole, 4-hydroxy-1-N-methylindole, 4-hydroxy-2-methylindole, 4-hydroxy-5-methylindole, 4-hydroxy-1-N-(β-hydroxyethyl)indole, 4-hydroxy-1-N-(β-hydroxypropyl)indole, 1-N-(β,γ-dihydroxypropyl)-4-hydroxyindole, 4-hydroxy-1-N-(β-hydroxyethyl)-5-methylindole, 1-N-(γ-dimethylaminopropyl)-4-hydroxyindole, and an addition salt thereof with an acid.

5. The composition according to claim 1, wherein the indoline derivatives are chosen from 4-hydroxyindoline, 6-hydroxyindoline, 6-aminoindoline, 5,6-dihydroxyindoline, and the addition salts thereof with an acid.

6. The composition according to claim 1, wherein the benzimidazole derivatives are chosen from compounds corresponding to formula (II), and an addition salt thereof with an acid:

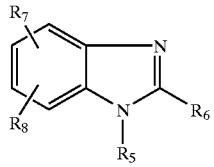

(II)

in which:
$R_5$ is chosen from hydrogen and $C_1$–$C_4$ alkyl radicals,
$R_6$ is chosen from hydrogen, $C_1$–$C_4$ alkyl radicals, and a phenyl radical,
$R_7$ is chosen from a hydroxyl radical, an amino radical and a methoxy radical,
$R_8$ is chosen from hydrogen, a hydroxyl radical, a methoxy radical, and $C_1$–$C_4$ alkyl radicals;
provided that:
(a) when $R_7$ is an amino radical, it is at ring position 4,
(b) when $R_7$ is at ring position 4, then $R_8$ is at ring position 7, and
(c) when $R_7$ is at ring position 5, then $R_8$ is at ring position 6.

7. The composition according to claim 6, wherein the benzimidazole derivatives of formula (II) are chosen from 4-hydroxybenzimidazole, 4-aminobenzimidazole, 4-hydroxy-7-methylbenzimidazole, 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole, 5,6-dimethoxybenzimidazole, and an addition salt thereof with an acid.

8. The composition according to claim 1, wherein the benzomorpholine derivatives are chosen from compounds corresponding to formula (III), and an addition salt thereof with an acid:

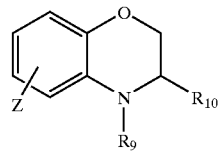

(III)

in which:
$R_9$ and $R_{10}$, which may be identical or different, are chosen from hydrogen and $C_1$–$C_4$ alkyl radicals, and
Z is chosen from a hydroxyl radical or an amino radical.

9. The composition according to claim 8, wherein the benzomorpholine derivatives of formula (III) are chosen from 6-hydroxy-1,4-benzomorpholine, N-methyl-6-hydroxy-1,4-benzomorpholine, 6-amino-1,4-benzomorpholine, and an addition salt thereof with an acid.

10. The composition according to claim 1, wherein the sesamol derivatives are chosen from compounds corresponding to formula (IV), and an addition salt thereof with an acid:

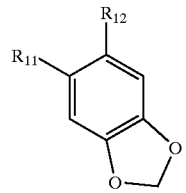

(IV)

in which:
$R_{11}$ is chosen from a hydroxyl radical, an amino radical, ($C_1$–$C_4$)alkylamino radicals, monohydroxy($C_1$–$C_4$) alkylamino radicals, and polyhydroxy($C_2$–$C_4$) alkylamino radicals, and
$R_{12}$ is chosen from hydrogen, halogen atoms, and $C_1$–$C_4$ alkoxy radicals.

11. The composition according to claim 10, wherein the sesamol derivatives of formula (IV) are chosen from 2-bromo-4,5-methylenedioxyphenol, 2-methoxy-4,5-methylenedioxyaniline, 2-(β-hydroxyethyl)amino-4,5-methylenedioxybenzene, and an addition salt thereof with an acid.

12. The composition according to claim 1, wherein the pyrazoloazole derivatives are chosen from [2-methylpyrazolo[1,5-b]-1,2,4-triazole, 2-ethylpyrazolo[1,5-b]-1,2,4-triazole, 2-isopropylpyrazolo[1,5-b]-1,2,4-triazole, 2-phenylpyrazolo[1,5-b]-1,2,4-triazole, 2,6-dimethylpyrazolo[1,5-b]-1,2,4-triazole, 7-chloro-2,6-dimethylpyrazolo[1,5-b]-1,2,4-triazole, 3,6-dimethylpyrazolo[3,2-c]-1,2,4-triazole, 6-phenyl-3-methylthiopyrazolo[3,2-c]-1,2,4-triazole, 6-aminopyrazolo[1,5-a]benzimidazole] 2-methylpyrazolo(1,5-b)-1,2,4-triazole, 2-ethylpyrazolo(1,5-b)-1,2,4-triazole, 2-isopropylpyrazolo(1,5-b)-1,2,4-triazole, 2-phenylpyrazolo(1,5-b)-1,2,4-triazole, 2,6-dimethylpyrazolo(1,5-b)-1,2,4-triazole, 7-chloro-2,6-dimethylpyrazolo(1,5-b)-1,2,4-triazole, 3,6-dimethylpyrazolo(3,2-c)-1,2,4-triazole, 6-phenyl-3-methylthiopyrazolo(3,2-c)-1,2,4-triazole, 6-aminopyrazolo(1,5-a)benzimidazole, and an addition salt thereof with an acid.

13. The composition according to claim 1, wherein the pyrroloazole derivatives are chosen from [5-cyano-4-ethoxycarbonyl-8-methylpyrrolo[1,2-b]-1,2,4-triazole, 5-cyano-8-methyl-4-phenylpyrrolo[1,2-b]-1,2,4-triazole, 7-amido-6-ethoxycarbonylpyrrolo[1,2-a]benzimidazole] 5-cyano-4-ethoxycarbonyl-8-methylpyrrolo(1,2-b)-1,2,4-triazole, 5-cyano-8-methyl-4-phenylpyrrolo(1,2-b)-1,2,4-triazole, 7-amido-6-ethoxycarbonylpyrrolo(1,2-a)benzimidazole, an addition salt thereof with an acid.

14. The composition according to claim 1, wherein the imidazoloazole derivatives are chosen from 7,8-dicyanoimidazolo(3,2-a)imidazole, 7,8-dicyano-4-methylimidazolo(3,2-a)imidazole, and an addition salt thereof with an acid.

15. The composition according to claim 1, wherein the pyrazolopyrimidine derivatives are chosen from [pyrazolo[1,5-a]pyrimidin-7-one, 2,5-dimethylpyrazolo[1,5-a]pyrimidin-7-one, 2-methyl-6-ethoxycarbonylpyrazolo[1,5-a]pyrimidin-7-one, 2-methyl-5-methoxymethylpyrazolo[1,5-a]-pyrimidin-7-one, 2-tert-butyl-5-trifluoromethylpyrazolo[1,5-a]pyrimidin-7-one, 2,7-dimethylpyrazolo[1,5-a]pyrimidin-5-one], pyrazolo(1,5-a)pyrimidin-7-one, 2,5-dimethylpyrazolo(1,5-a)pyrimidin-7-one, 2-methyl-6-ethoxycarbonylpyrazolo(1,5-a)pyrimidin-7-one, 2-methyl-5-methoxymethylpyrazolo(1,5-a)- pyrimidin-7-one, 2-tert-butyl-5-trifluoromethylpyrazolo(1, 5-a)pyrimidin-7-one, 2,7-dimethylpyrazolo(1,5-a)pyrimidin-5-one, and an addition salt thereof with an acid.

16. The composition according to claim 1, wherein the pyrazoline-3,5-dione derivatives are chosen from 1,2-diphenylpyrazoline-3,5-dione, 1,2-diethylpyrazoline-3,5-dione, and an addition salt thereof with an acid.

17. The composition according to claim 1, wherein the pyridine couplers are chosen from 3-(3',5'-diamino-2'-pyridyloxy)-2-hydroxypropanol, the pyridine derivatives corresponding to formula (V), and an addition salt thereof with an acid:

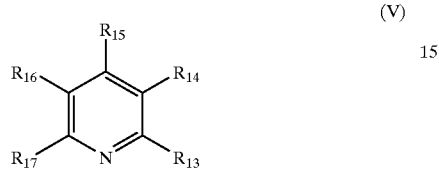

(V)

in which:
R$_{13}$ is chosen from hydrogen, a hydroxyl radical, an amino radical, and an —OCH$_2$CH$_2$COCH$_2$CH$_2$OH radical,
R$_{14}$ and R$_{,16}$, which may be identical or different, are chosen from hydrogen, a hydroxyl radical, an amino radical, and C$_1$–C$_4$ alkyl radicals,
R$_{15}$ is chosen from hydrogen and C$_1$–C$_4$ alkyl radicals,
R$_{17}$ is chosen from hydrogen, a hydroxyl radical, and an amino radical;
provided that the pyridine derivatives of formula (V) do not comprise more than (a) two amino groups,
(b) two hydroxyl groups;
(c) one amino group and one hydroxyl group, wherein the amino and/or hydroxyl groups are in a meta position relative to each other.

18. The composition according to claim 17, wherein the pyridine derivatives of formula (V) are chosen from 2,6-dihydroxy-4-methylpyridine, 2,6-dihydroxy-3,4-dimethylpyridine, 2,6-diaminopyridine, 3-oxo-5-(3',5'-diamino-2'-pyridyloxy)pentanol, 3-(3',5'-diamino-2'-pyridyloxy)-2-hydroxypropanol, and an addition salt thereof with an acid.

19. The composition according to claim 1, wherein the oxidation base is chosen from a para-phenylenediamine, a double base, a para-aminophenol, an ortho-aminophenol, and a heterocyclic oxidation base.

20. The composition according to claim 1, wherein the oxidation base is present in said composition in an amount ranging from 0.0005 to 12% by weight relative to the total weight of the composition.

21. The composition according to claim 20, wherein the oxidation base is present in said composition in an amount ranging from 0.005 to 6% by weight relative to the total weight of the composition.

22. The composition according to claim 1, wherein the first coupler is present in said composition in an amount ranging from 0.001 to 10% by weight relative to the total weight of the composition.

23. The composition according to claim 22, wherein the first coupler is present in said composition in an amount ranging from 0.01 to 5% by weight relative to the total weight of the composition.

24. The composition according to claim 1, wherein the second coupler is present in said composition in an amount ranging from 0.0001 to 10% by weight relative to the total weight of the composition.

25. The composition according to claim 24, wherein the second coupler is present in said composition in an amount ranging from 0.005 to 5% by weight relative to the total weight of the composition.

26. The composition according to claim 1, wherein the addition salt with an acid is chosen from a hydrochloride, a hydrobromide, a sulphate, a tartrate, a lactate, and an acetate.

27. The composition according to claim 2, where in the human keratin fibres are hair.

28. A composition for the oxidation dyeing of keratin fibres comprising, in a medium which is suitable for dyeing:
(a) at least one oxidation base chosen from para-phenylenediamines, double bases, ortho-aminophenols, heterocyclic oxidation bases, para-aminophenols corresponding to formula (VIII) and the addition salts thereof,

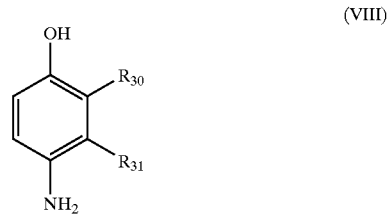

(VIII)

wherein:
R$_{30}$ is chosen from hydrogen, halogen, (C$_1$–C$_4$) alkyl groups, (C$_1$–C$_4$) monohydroxyalkyl groups, (C$_1$–C$_4$) alkoxy(C$_1$–C$_4$)alkyl groups, (C$_1$–C$_4$) aminoalkyl groups, and hydroxy(C$_1$–C$_4$)alkylamino(C$_1$–C$_4$) alkly groups,
R$_{31}$ is chosen from hydrogen, halogen, (C$_1$–C$_4$) alkyl groups, (C$_1$–-C$_4$)monohydroxyalkyl groups, (C$_2$–C$_4$) polyhydroxyaklyl groups, (C$_1$–C$_4$) aminoalkyl groups, cyano(C$_1$–C$_4$)alkyl groups, and (C$_1$–C$_4$)alkoxy(C$_1$–C$_4$)alkyl groups,
wherein at least one of the radicals R$_{30}$ and R$_{31}$ is hydrogen, and
(b) at least two couplers, wherein
the first coupler is chosen from 1,3-bis(β-hydroxyethyl)amino-2-methylbenzene and an acid addition salt thereof; and
the second coupler is chosen from a heterocyclic coupler chosen from indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo(2,3-d)oxazole derivatives, pyrazolo(3,4-d)thiazole derivatives, thiazoloazole S-oxide derivatives, thiazoloazole S,S-dioxide derivatives, pyridine derivatives and the addition salts thereof with an acid,
provided that if said dye composition contains at least one oxidation base chosen from a pyrimidine base, 2-β-hydroxyethyl-para-phenylenediamine, and an acid addition salt thereof, then the heterocyclic coupler is other than a pyridine coupler.

29. A process for dyeing keratin fibres comprising the steps of 1) applying to said fibres at least one dye composition, and 2) developing color of the keratin fibres at acidic, neutral or alkaline pH by adding an oxidizing agent which is added to the dye composition at the time of applying to said fibres, or wherein the oxidizing agent is present in an oxidizing composition that is applied simultaneously with the dye composition or sequentially after application of the dye composition, said at least one dye composition comprising, in a medium which is suitable for dyeing:

(a) at least one oxidation base, (b) and at least two couplers wherein the first coupler is chosen from 1,3-bis(β-hydroxyethyl) amino-2-methylbenzene and an addition salt thereof with an acid, and the second coupler is chosen from a heterocyclic coupler chosen from indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo(2,3-d)oxazole derivatives, pyrazolo(3,4-d)thiazole derivatives, thiazoloazole S-oxide derivatives, thiazoloazole S,S-dioxide derivatives, pyridine derivatives and the addition salts thereof with an acid, provided that if said dye composition contains an oxidation base chosen from a pyrimidine base, 2-β-hydroxyethyl-para-phenylenediamine, and an addition salt thereof with an acid, then the heterocyclic coupler is other than a pyridine coupler.

30. The process according to claim 29, wherein the oxidizing agent present in the oxidizing composition is chosen from hydrogen peroxide, urea peroxide, an alkali metal bromate, a persalt, a peracid, and an enzyme.

31. The process according to claim 30, wherein the persalt is chosen from a perborate, a percarbonate, and a persulphate.

32. The process according to claim 29, wherein the keratin fibres are human keratin fibres.

33. The process according to claim 32, wherein the human keratin fibres are hair.

34. A multi-compartment dyeing kit comprising a first compartment that contains a dye composition for the oxidation dyeing of keratin fibres comprising, in a medium which is suitable for dyeing:

(a) at least one oxidation base, (b) and at least two couplers wherein the first coupler is chosen from 1,3-bis(β-hydroxyethyl)amino-2-methylbenzene and an addition salt thereof with an acid, and the second coupler is chosen from a heterocyclic coupler chosen from indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo(2,3-d)oxazole derivatives, pyrazolo(3,4-d)thiazole derivatives, thiazoloazole S-oxide derivatives, thiazoloazole S,S-dioxide derivatives, pyridine derivatives and the addition salts thereof with an acid, provided that if said dye composition contains an oxidation base chosen from a pyrimidine base, 2-β-hydroxyethyl-para-phenylenediamine, and an addition salt thereof with an acid, then the heterocyclic coupler is other than a pyridine coupler, and a second compartment that contains an oxidizing composition.

* * * * *

UNITED STATES PATENT AND TRADEMARK OFFICE
CERTIFICATE OF CORRECTION

PATENT NO.    : 6,395,042 B1
DATED         : May 28, 2002
INVENTOR(S)   : Marie-Pascale Audousset It is certified that error appears in the above-identified patent and that said Letters Patent is hereby corrected as shown below:

Column 14,
Line 3, "1,3-bis(2-hydroxyethyl)" should read -- 1,3-bis(ß-hydroxyethyl) --

Column 16,
Lines 26-32, delete in their entirety.
Line 33, delete "[1,5-a]benzimidazole]".
Line 44, delete "[5-cyano-4-".
Lines 45-47, delete in their entirety.
Line 58, delete "[pyrazolo".
Lines 59-63, delete in their entirety.
Line 64, delete "dimethylpyrazolo[1,5-a]pyrimidin-5-one]"

Column 17,
Line 25, "$R_{,16,}$" should read -- $R_{16}$, --.

Column 18,
Line 35, "$(C_1\text{---}C_4)$" should read -- $(C_1\text{-}C_4)$ --.

Signed and Sealed this

Sixth Day of August, 2002

Attest:

JAMES E. ROGAN
Attesting Officer    Director of the United States Patent and Trademark Office